(12) United States Patent
Sander

(10) Patent No.: US 10,960,055 B2
(45) Date of Patent: *Mar. 30, 2021

(54) SCARRING REDUCING WOUND TREATMENT

(71) Applicant: MÖLNLYCKE HEALTH CARE AB, Gothenburg (SE)

(72) Inventor: Michael Sander, Werther (DE)

(73) Assignee: MÖLNLYCKE HEALTH CARE AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/909,038

(22) Filed: Jun. 23, 2020

(65) Prior Publication Data

US 2020/0316176 A1    Oct. 8, 2020

Related U.S. Application Data

(63) Continuation of application No. 15/056,539, filed on Feb. 29, 2016, now Pat. No. 10,729,748, which is a continuation-in-part of application No. 14/370,628, filed as application No. PCT/EP2013/050374 on Jan. 10, 2013, now abandoned.

(30) Foreign Application Priority Data

Jan. 13, 2012   (EP) .................................... 12000176

(51) Int. Cl.
| | | |
|---|---|---|
| A61K 38/42 | (2006.01) |
| A61Q 19/00 | (2006.01) |
| A61K 8/64 | (2006.01) |
| A61K 9/00 | (2006.01) |
| A61L 15/40 | (2006.01) |
| A61L 26/00 | (2006.01) |
| A61L 15/44 | (2006.01) |
| A61K 9/12 | (2006.01) |
| A61K 47/20 | (2006.01) |

(52) U.S. Cl.
CPC ................ *A61K 38/42* (2013.01); *A61K 8/64* (2013.01); *A61K 9/0014* (2013.01); *A61K 9/12* (2013.01); *A61K 47/20* (2013.01); *A61L 15/40* (2013.01); *A61L 15/44* (2013.01); *A61L 26/0066* (2013.01); *A61Q 19/00* (2013.01)

(58) Field of Classification Search
None
See application file for complete search history.

(56) References Cited

U.S. PATENT DOCUMENTS

| 4,776,991 A | 10/1988 | Farmer et al. |
| 5,874,093 A | 2/1999 | Eliaz et al. |
| 5,985,332 A | 11/1999 | Barnikol et al. |
| 2003/0180365 A1 | 9/2003 | Barnikol |
| 2005/0129747 A1 | 6/2005 | Barnikol et al. |
| 2010/0278887 A1 | 11/2010 | Zal et al. |
| 2010/0311657 A1 | 12/2010 | Abuchowski et al. |

FOREIGN PATENT DOCUMENTS

| EP | 2550973 | 1/2013 |
| FR | 2917292 | 12/2008 |
| WO | 9715313 | 5/1997 |
| WO | 0205754 | 1/2002 |
| WO | 2008034138 | 3/2008 |

OTHER PUBLICATIONS

"Aerosols", Available online at: http://aerosolsucp.blogspot.com/, Mar. 31, 2008, 8 pages.
Adzick et al., "Cells, Matrix, Growth Factors, and the Surgeon. The Biology of Scarless Fetal Wound Repair", Annals of Surgery, vol. 220, No. 1, 1994, pp. 10-18.
Amberson et al., "Clinical experience with hemoglobin-saline solutions", J Appl Physiol, 1949, pp. 469-489.
Arenberger et al., "Clinical results of the application of a hemoglobin spray to promote healing of chronic wounds", GMS Krankenhaushygiene Interdisziplinar, vol. 6(1), 2011, pp. 1-9.
Arenbergerova et al., "Effect of topical haemoglobin on healing in patients with venous leg ulcers", Der Hautarzt,, 2013, pp. 1-7.
Bateman, "Topical haemoglobin spray for diabetic foot ulceration", British Journal of Nursing (Tissue Viability Supplement), vol. 24, No. 12, 2015, pp. S20-S25.
Chadwick et al., "International Best Practice Guidelines: Wound Management in Diabetic Foot Ulcers,", Wounds International, 2013, pp. 1-23.
Collier, "Oxygen affinity of human blood in presence of carbon monoxide", J Appl Physiol, 40(3), 1976, pp. 487-490.
Ding et al., "The Role of Chemokines in Fibrotic Wound Healing", Advances in Wound Care, vol. 4, No. 11, 2015, pp. 673-686.
Ferguson et al., "Scar-free healing: from embryonic mechanisms to adult therapeutic intervention", Phil. Trans. R. Soc. Land. B 359, 2004, pp. 839-850.
Gauglitz et al., "Hypertrophic Scarring and Keloids: Pathomechanisms and Current and Emerging Treatment Strategies", Mol. Med. 17(1-2), 2011, pp. 113-125.
Guzman, "Carbon monoxide poisoning", Crit Care Clin, 28(4), 2012, p. 537-548.
Henkel-Hanke et al., "Artificial Oxygen Carriers: A current Review", AANA Journal, vol. 75, No. 3, Jun. 2007, pp. 205-2011.
Hunt, "Topical oxygen-haemoglobin use on sloughy wounds: positive patient outcomes and the promotion of self-care", Wounds UK, vol. 11, No. 4, 2015, pp. 90-95.
Jahr et al., "Hemoglobin-Based Oxygen Carriers: History, Limits, Brief Summary of the State of the Art, Including Clinical Trials", Chemistry and Biochemistry of Oxygen Therapeutics, 2011, pp. 301-316.

(Continued)

*Primary Examiner* — James H Alstrum-Acevedo
*Assistant Examiner* — Tara L Martinez
(74) *Attorney, Agent, or Firm* — Kilpatrick Townsend & Stockton LLP

(57) ABSTRACT

Undue scarring of healing wounds is decreased and/or the relapse rate of wounds is lowered by applying a composition that includes hemoglobin to the wound area. At least 40% of the hemoglobin in the composition is provided in CO-charged form.

13 Claims, No Drawings

(56) References Cited

OTHER PUBLICATIONS

Jones, "Winter's concept of moist wound healing: a review of the evidence and impact on clinical practice", Journal of Wound Care, vol. 14, 2005, pp. 273-276.

Martin et al., "Cellular and molecular mechanisms of repair in acute and chronic wound healing", British Journal of Dermatology 173, 2015, pp. 370-378.

Mustoe et al., "International Clinical Recommendations on Scar Management", Plastic and Reconstructive Surgery, vol. 110, No. 2, 2002, pp. 560-571.

Omaye, "Metabolic modulation of carbon monoxide toxicity", Toxicology,180(2), 2002, pp. 139-150.

Page, "Oxygen transport by erythrocyte/hemoglobin solution mixtures in an in vitro capillary as a model of hemoglobin-based oxygen carrier performance", Microvasc Res., 55(1 ), 1998, pp. 54-64.

Petri et al., "Photoacoustic imaging of real-time oxygen changes in chronic leg ulcers after topical application of a haemoglobin spray: a pilot study", Journal of Wound Care, vol. 25, No. 2, 2016, pp. 1-5.

Russell, "Blood carboxyhaemoglobin changes during tobacco smoking", Postgrad Med J, 49(576), 1973, pp. 684-687.

Sakai et al., "Characteristics of Bovine Hemoglobin as a Potential Source of Hemoglobin—Vesicles for an Artificial Oxygen Carrier", Journal of Biochemistry, vol. 131, No. 4, 2002, pp. 611-617.

Scholander, "Oxygen transport through hemoglobin solutions", Science, 131 (3400), 1960, pp. 585-590.

Sellards et al., "Injection of Hemoglobin in Man and its Relations to Blood Destruction, with Especial Reference to the Anemias", 1917, pp. 469-494.

Silverman et al., "Hemoglobin-based oxygen carriers: current status and future directions", Transfusion, 49(11), 2009, pp. 2495-2515.

Silverstein, "Smoking and wound healing", Am J Med, 93(1a), 1992, pp. 22s-24s.

Singer et al., "Cutaneous wound healing", N Engl J Med, 341(10), 1999, pp. 738-746.

Sloan et al., "The effects of smoking on fracture healing", Surgeon, 8(2), 2010, pp. 111-116.

Tiwari, "Burn Wound: How it Differs from other Wounds?", Indian Journal of Plastic Surgery, vol. 45 No. 2, 2012, pp. 364-373.

Tziotzios et al., "Cutaneous Scarring: Pathophysiology, Molecular Mechanisms, and Scar Reduction Therapeutics", Journal of the American Academy of Dermatology, vol. 66, Issue 1, Jan. 2012, pp. 13-24.

Weiskopf, "Introduction", Chemistry and Biochemistry of Oxygen Therapeutics, 2011, pp. 1-7.

Wu et al., "Carbon monoxide: endogenous production, physiological functions, and pharmacological applications", Pharmacal Rev., vol. 57, issue 4, Dec. 2005, pp. 585-630.

SCARRING REDUCING WOUND TREATMENT

RELATED APPLICATIONS

This application is a continuation of U.S. patent application Ser. No. 15/056,539, filed Feb. 29, 2016, entitled "SCARRING REDUCING WOUND TREATMENT", which is a continuation-in-part of U.S. patent application Ser. No. 14/370,628, filed Jul. 3, 2014, entitled "SCARRING REDUCING WOUND TREATMENT," which is the U.S. National Phase under 35 U.S.C. § 371 of International Application PCT/EP2013/050374, filed Jan. 10, 2013, which claims priority to EP 12000176.3, filed Jan. 13, 2012, each of which is incorporated herein by reference in its entirety.

BACKGROUND

Field

The present invention refers to the use of hemoglobin or myoglobin, preferably a hemoglobin or myoglobin charged with a non-oxygen ligand for improved scarring of wounds.

Description of the Related Technology

Different methods are used for treating wounds, depending on their status. First, a wound that is still open preferably should be disinfected and thereby protected against negative external influences. This can be done by means of suitable disinfectant solutions or spray-on bandages or also by applying iodine solution. Actual wound healing must then take place from inside. This means that the blood vessels still in place must supply the destroyed tissue with sufficient amounts of substrates, so that the tissue repair mechanism can start.

Wounds can be caused by various factors, like e.g. injuries or also after operations or traumatic events.

On the other hand, it is known that wound formation, particularly also chronic wounds, can also be provoked by diseases, in which degeneration and/or constriction of large and/or small blood vessels occurs. This may be the result e.g. in the case of older patients, of extended stays in bed (decubitus) or of diabetes mellitus which may lead to degeneration and arteriosclerosis (P. Carpenter, A. Franco, Atlas der Kapillaroskopie [Atlas of Capillaroscopy], 1983, Abbott, Max-Planck-Inst. 2, D-Wiesbaden) of the large and small blood vessels (macroangiopathy and microangiopathy of the arteries). It was also shown that an oxygen deficiency (hypoxia) is present in the wound area. 40 mmHg is considered to be a critical value (C. D. Muller et al., Hartmann Wund [Wound] Forum 1 (1999), 17-25).

The blood flows to the tissues, including the skin, through the arteries and supplies the cells with substrates required for life. Any degeneration of the blood vessels results in a deficient supply of substrates to the cells, leading to their death. The substrates must pass the last, seemingly insignificant gap of approximately 20 μm from the smallest blood vessels (capillaries) to the cells by diffusion; in this connection, oxygen plays a special role, because it is difficult for the organism to handle this substrate.

There are three main problems involved: (1) It is true that oxygen is absolutely essential for life (a human being is brain-dead after only approximately five minutes if his/her brain does not receive oxygen), but at the same time, oxygen is highly toxic (a newborn that receives respiration treatment with pure oxygen will die-after only a few days). (2) Oxygen has very little solubility in an aqueous medium; this results, according to FICK's first law, in a lower diffusion rate of oxygen. In addition, there is a fundamental law of diffusion, namely SMOLUCHOWSKI's and EINSTEIN's law, that states that the diffusion speed (of oxygen) decreases with an increasing diffusion distance. Now the diffusion constant of oxygen is so low that the diffusion speed at a diffusion distance of as little as 20 μm is only 5% of the initial value. A water layer of e.g. 50 μm represents nearly complete oxygen insulation for the cells. Oxygen is transported along the long paths in the organism from the lungs to the tips of the toes with the bloodstream, bound to hemoglobin, and only in this way is able to overcome the long distances in a manner that is suitable for the organism. (3) For oxygen, in contrast to glucose, for example, there is no storage area in the body, therefore this substrate must be available to the cells at all times and quickly, in a sufficient amount; oxygen is a so-called immediate substrate necessary for life.

An intact organism has solved these problems by using several mechanisms. The toxic effects of oxygen are avoided in that the latter binds during transport to hemoglobin and thereby remains harmless. At the same time, the free oxygen is diluted and thereby further loses its harmful oxidative potential. Nevertheless, it is instantaneously available in a sufficient amount, because the binding to hemoglobin is reversible. The problem of the low diffusive range is solved in that the organism has developed a very finely branched blood vessel network (capillary network), which ensures that on the average, every cell is at a distance of at most 25 μm from a capillary; in this way, the diffusion path of oxygen in the organism remains below the critical length of 50 μm. In addition, a cell can be diffusively supplied with oxygen from several sides; this represents a safety mechanism. The immediate availability, in accordance with the demand (oxygen is not allowed to be available in excess, otherwise it would have a harmful effect) is achieved, in the organism, by means of vascular regulation of the blood vessel flow, which controls perfusion and thereby optimizes the supply of oxygen.

If there is an open wound surface, the oxygen supply to the cells is interrupted. The oxygen supply from air outside is poor because an aqueous liquid film is laying on the (tissue) cell layer, which film, as explained, forms a diffusive oxygen barrier. Fresh wounds in normal tissue can heal in a few days, if the oxygen supply from underneath, in other words from the inside, is sufficient. However, it was shown in animal experiments that even fresh wounds heal better if the oxygen concentration of the surrounding air is increased (M. P. Pal et al., Sug. Gyn. Obstet. 135 (1972), 756-758). Older, particularly chronic wounds are known to heal very slowly, if at all, due to their oxygen deficiency.

To heal chronic wounds better, as well, so-called hyperbaric oxygen therapy (HBO) has been used. In this treatment, patients are placed in pressurized chambers, where they are subjected to an excess pressure of pure oxygen of about 3 bars for a certain period of time (C. D. Muller et al., Hartmann Wund Forum 1 (1999), 17-25). In fact, wound healing may be increased by this method. However, the effect decreases with the number of treatments.

A further aspect of wound treatment is the avoidance of undue formation of scars. Scars may have aesthetical disadvantages and/or diminish sensitivity and supply of the concerned tissue. Scarring is increased and may be undue under non-sufficient oxygen supply of the wound area.

U.S. Pat. No. 2,527,210 describes a hemoglobin solution that can allegedly be used for the treatment of wounds, both intravenously and topically, for example by spraying. In this description, the hemoglobin is obtained from fresh erythrocytes that are subjected to freezing shock after centrifugation and drawing off the blood plasma fraction. This results in cell lysis, and hemoglobin is released. The broken cell walls are also present in the product. This formulation is a concentrated cell detritus (cell fragments). In this way, an antiseptic cover effect such as otherwise achieved with iodine solution, after having added 5% sodium sulfide, is supposed. In other words, the wound is merely closed. Oxygen transport is not mentioned there.

WO 97/15313 describes the therapeutic use of hemoglobin for improving wound healing. For this purpose, hemoglobin free of stroma and pyrogens is intravenously administered to the patients, particularly after operations and traumatic events to increase the blood pressure. In particular, hemoglobin cross-linked with diaspirin is used for this purpose.

WO 2003/077941 teaches the treatment of open wounds with a hemoglobin solution comprising isolated and optionally crosslinked hemoglobin. The solutions were freshly prepared with hemoglobin from pig blood and applied to chronic wounds.

During the preparation and storage of oxygen carriers on basis of hemoglobin or myoglobin they can lose their functionality partially or completely. To prevent this it is desirable to stabilize the oxygen carriers that they remain usable and able to transport oxygen.

Generally, there are different approaches to the preparation of artificial oxygen carriers; one of them is the preparation of suitable solutions of native or chemically modified hemoglobins (see "Issues from Vth International Symposium on Blood Substitutes, San Diego, Calif., USA, March 1993", Artificial Cells, Blood Substitutes, and Immobilization Biotechnology 22 (1994), vol. 2-vol. 4). One problem in the handling of such pharmaceutical preparations as artificial oxygen carriers is their increasing inactivation by spontaneous oxidation to methemoglobin which is no longer able to transport oxygen. This occurs usually during preparation by the producer and the subsequent storage.

Several approaches for solving this problem are described. Either it is tried to minimize the degree of oxidation of hemoglobin, or to reduce the oxidized hemoglobin back again.

One possibility for prevention of spontaneous oxidation is deoxygenating the hemoglobin (i.e., entirely removing oxygen from the preparation), since desoxyhemoglobin oxidizes much more slowly to methemoglobin than oxyhemoglobin.

Further it is possible to minimize the amount of oxidation by storage and/or preparation at the lowest possible temperature (for aqueous solutions, at about 4° C.).

Additionally, the rate of oxidation of hemoglobin depends on the hydrogen ion concentration, i.e., the pH. For example, for native human hemoglobin there is a minimum in the interval between pH 7.5 and 9.5.

Also, the addition of certain alcohols can diminish the oxidation of hemoglobin. Some of them work even in low concentration. One problem is the toxicity of these alcohols.

Certain metal ions ($Cu_2^+$, $Fe_3+$ etc.) catalyze the spontaneous oxidation of hemoglobin. They can be rendered ineffective by complexing with EDTA (ethylenediaminetetraacetic acid), although EDTA itself promotes the spontaneous oxidation of hemoglobin.

Protection of artificial oxygen carriers against oxidation may further be achieved by the addition of reducing substances. Under certain circumstances they even result in a reactivation of oxidized hemoglobin.

EP 0 857 733 describes that hemoglobin may be stabilized by binding a ligand, in particular carbon monoxide, to the oxygen binding site. It was found that such a carbonylhemoglobin can be applied to an organism without de-ligandation and is suitable as an oxygen carrier inside of the blood stream.

In DE 100 34 970 A1 it is mentioned that oxygen carriers as hemoglobin or myoglobin can be used in topical cosmetic emulsions for treatment of the skin in case of oxygen malnourishment.

Further cosmetic compositions are described for treatment of the skin, even in case of scarring, including an increased free oxygen content, like e.g. U.S. Pat. No. 5,874,093; U.S. 2003/0083610 A1 or U.S. 2005/0244354 A1.

A method for wound care and treatment resulting in decreased scarring in a wound by applying a gas-enriched fluid (in particular an oxygen-enriched fluid) is described in WO 08/115290.

SUMMARY OF CERTAIN INVENTIVE ASPECTS

The object of the present invention is to provide a product for the external treatment of wounds, which decreases undue scarring of a wound area, resulting in smooth, elastic, resilient tissue, is easy in handling and preferably storable.

This object is met, according to the invention, by the use of an oxygen carrier, preferably hemoglobin or myoglobin, in a method for reducing undue scarring of a wound or wound area and/or for lowering the relapse rate of wounds, in particular of chronic wounds, and by the use of a composition, comprising (a) an oxygen carrier, preferably hemoglobin or myoglobin, and (b) at least one further ingredient, selected from electrolyte(s) preservative(s), stabilizer(s), anti-flocculant(s), anticoagulant(s), pH buffering agent(s), solvent(s), antioxidant(s), film-forming agent(s) and crosslinking agent(s) in a method for reducing undue scarring of a wound or wound area and/or for lowering the relapse rate of wounds, in particular of chronic wounds.

DETAILED DESCRIPTION OF CERTAIN EMBODIMENTS

In a preferred embodiment of the invention in at least 40% of said oxygen carriers the oxygen binding site is charged by a non-02 ligand.

According to the invention preferably a natural (native) oxygen carrier, particularly hemoglobin or myoglobin or a modified derivative thereof, or mixtures thereof, is/are used. Hemoglobin or myoglobin of human or animal origin, in particular of equine, bovine or preferably porcine origin, is particularly suitable for the present invention. Human or porcine hemoglobin, which is natural or modified as described below, is particularly preferred as an oxygen carrier. The oxygen carrier may be freshly isolated from human or animal blood or may be artificially prepared.

Mixtures of natural and modified oxygen carrier can also be used, such as, for example, in a ratio of 20:1 to 1:20, with reference to weight. Further, mixtures of hemoglobin and myoglobin, or their modified derivatives may be used in the aforementioned ratio of 20:1 to 1:20.

In a further embodiment the oxygen carrier may be modified. The modification can be an intramolecular cross-linking, polymerization (intermolecular cross-linking), pegylation (covalent linking with polyalkylene oxides), modification with chemically reactive effectors such as pyridoxal-5'-phosphate or 2-nor-2-formyl-pyridoxal-5'- phosphate, or also with chemically non-reactive effectors of the oxygen bond, such as 2,3-bisphosphoglycerate, inositol hexaphosphate, inositol hexasulfate, or mellitic acid, or a combination thereof. Such modifications are known and described, for example, in DE-A 100 31 744, DE-A 100 31 742, and DE-A 100 31 740. Cross-linking of oxygen carriers is also described in DE 197 01 37, EP 97 1000790, DE 44 18 937, DE 38 41 105, DE 37 14 351, DE 35 76 651.

Examples for modified oxygen carriers are hemoglobins having a molecular weight of 65,000 to 15,000,000, such as intramolecularly cross-linked molecules according to WO 97/15313, particularly polymer products as well as intermolecularly cross-linked products having an average molecular weight of 80,000 to 10,000,000 g/mol, particularly 100,000 to 5,000,000, or analogously produced myoglobins having a molecular weight of 16,000 to 5,000,000, particularly 100,000 to 3,000,000, preferably 1,000,000 g/mol. Those oxygen carriers that are polymerized, for example using cross-linking agents known for intermolecular modification, such as bifunctional cross-linking agents like butadiene diepoxy, divinyl sulfone, diisocyanate, particularly hexamethylene diisocyanate, cyclohexyl diisocyanate, and 2,5-bisisocyanatobenzol sulfonic acid, di-N-hydroxy succinimidyl ester, diimidoester, or dialdehyde, particularly glyoxal, glycol aldehyde that reacts analogously, or glutardialdehyde may be used.

Furthermore, products which are polymerized in this manner and pegylated with a polyethylene glycol or suitable derivatives thereof may be used. This includes, for example, polyethylene oxide, polypropylene oxide, or a copolymer of ethylene oxide and propylene oxide, or an ester, ether, or ester amide thereof. It may be suitable if the covalently linked polyalkylene oxide has a molar mass of 200 to 5000 g/mol.

For covalent linking of the polyalkylene oxides, those derivatives of polyalkylene oxide that contain a linking agent already covalently bound with a functional group, thereby allowing a direct chemical reaction with amino, alcohol, or sulfhydryl groups of the hemoglobins, forming covalent links of the polyalkylene oxides may be suitable, for example polyalkylene oxides with reactive N-hydroxy succinimidyl ester, epoxy (glycidyl ether), ldehyde, isocyanate, vinyl sulfone, iodacetamide, imidazolyl formate, tresylate groups, and others. Many such monofunctionally activated polyethylene glycols are commercially available.

If modified oxygen carriers are used, modified cross-linked (intramolecular or intermolecular), or cross-linked and pegylated hemoglobin products having an average molecular weight of 250,000 to 750,000 g/mol, or myoglobin products having an average molecular weight of 50,000 to 750,000 g/mol, are preferred.

According to the particular preferred embodiment freshly isolated hemoglobin or myoglobin of human or animal origin, in particular of porcine origin is used for the treatment of wounds and/or for preparation of the inventive composition.

In a particular preferred embodiment of the present invention at least 40% of the oxygen binding sites of the oxygen carrier are charged with a non-O2 ligand. Preferably at least 50%, preferably at least 60%, more preferred at least 70%, even more preferred at least 80%, particularly preferred at least 90% or 95% of the hemoglobin or myoglobin is provided in ligand-charged form. This charge may already be applied during isolation of the carrier or after its further purification, however, it is particularly preferred to carry out the isolation of the oxygen carrier in its protected form, which means that during isolation or purification the ligand is provided to/contacted with the oxygen carrier.

The non-$O_2$ ligand preferably is carbon monoxide (CO) or nitrogen monoxide (NO) or a mixture thereof. Both ligands have a high affinity for the hemoglobin/myoglobin $O_2$ binding site(s) and serve as a protector against oxidation of the central $Fe3+$ Ion of the heme.

The charged oxygen carrier(s) is/are preferably dissolved in an aqueous or organic medium, wherein an aqueous solution is preferred, in an amount of 0.1 to 35 wt.-%, preferably 0.1 to 20 wt.-%, more preferred 0.1 to 15 wt.-%, to be ready for application.

A composition according to the present invention preferably further comprises at least one further additive, preferably selected from the group comprising electrolyte(s), stabilizer(s), anti-flocculant(s), preservative(s), pH buffering agent(s), solvent(s), antioxidant(s) and film-forming agent(s), more preferred selected from electrolyte(s), stabilizer(s), anti-flocculant(s), preservative(s) and pH buffering agent(s). Most preferred the composition is in form of a solution and comprises at least an electrolyte and optionally a stabilizer.

The solution may comprise physiologically compatible electrolytes, such as salts, in suitable or desired amounts. The electrolytes may be present in amounts of 0.1 to 30 wt.-%, preferably 0.1 to 10%, but preferably are present in a physiological concentration, respectively. Preferably the composition comprises a salt in the before mentioned amounts, like e.g. NaCl, KCl, $NH_4Cl$, $CaCO_3$, $Na_2CO_3$, $K_2CO_3$, $MgSO_4$, $Na_2SO_4$, $CaCl_2$, $MgCl_2$, sodium citrate, sodium lactate or mixtures of the mentioned or similar without being restricted to these examples. The most preferred salt is NaCl, particularly in a concentration of 0.9% (isotonic solution).

According to the invention it is particularly preferred that the composition comprises a compound acting as a stabilizer and/or anti-flocculant for proteins in particular for the hemoglobin/myoglobin, such as N-acetyl cysteine, cysteine, N-actyl methionine, methionine, non-chaotropic salts, polyols, like sugars, preferably disaccharides, and amino acids preferably each in amounts of 0.001 wt.-% to 20 wt.-%.

The polyols which may be employed are preferably low molecular weight polyols although polymeric derivatives may be employed. Such polyols include ethylene glycol, glycerol, erythritol and mannitol. Cyclic polyols which may be employed incorporate one or more alicyclic rings and may have at least one side chain. Preferred polyols include disaccharides and sugar alcohols, for example lactitol, sorbitol and inositol. Compounds having 2 to 10 hydroxyl groups are preferred. The amount of the polyol may be in the preferred range 0.001 to 20% more preferably 1 to 15% most preferably 2 to 10% w/v.

Further the protein stabilizer additive may be selected from a tris(hydroxymethyl)methyl compound of formula 1; $(HOCH_2)_3C-R$ (1) wherein R is: $C_1$-$C_4$ alkyl, substituted $C_1$-$C_4$ alkyl, $NH_2$, $NHC(CH_2OH)_3$, $C_1$-$C_4$ hydroxyalkyl; $C_1$-$C_4$ alkyl carboxylate, $NR^1R^2$ (wherein $R^1$ and $R^2$ may be independently: H, $C_1$-$C_4$ alkyl, $C_1$-$C_4$ alkyl sulphonate, $C_1$-$C_4$ hydroxyalkyl sulphonate). Examples of preferred compounds of formula (1) include: tris(hydroxymethyl)ethane; 1,1',1"-tris(hydroxymethyl)propane; tris(hydroxymethyl)aminomethane or salts thereof for example chloride, maleate, phosphate, succinate salts; 1,3 bis [tris(hydroxymethyl)methylamino]propane; bis(2hydroxyethyl)amino-tris (hydroxymethyl)methane; N [tris(hydroxymethyl)methyl]-2-aminoethane sulphonate; N [tris(hydroxymethyl)methyl]-3-aminopropane sulphonate; N [tris(hydroxymethyl)

methyl]-3-amino-2-hydroxypropane sulphonate; N-[tris (hydroxymethyl)methyl]-glycine. Said compounds as well may be added in the preferred range of 0.001 to 20% more preferably 1 to 15% most preferably 2 to 10% w/v.

Further the protein stabilizer additive may be selected from a polyelectrolyte. The polyelectrolyte may be a cationic or anionic polyelectrolyte. Amphoteric polyelectrolytes may also be employed. The cationic polyelectrolyte is preferably a polymer with cationic groups distributed along the molecular chain.

The cationic groups, which are preferably quaternary ammonium derived functions, may be disposed in side groups pendant from the chain or may be incorporated in it. Examples of cationic polyelectrolytes include: Copolymers of vinyl pyrollidone and quaternary methyl methacrylate ege.g. Gafquat series (755N, 734, HS-100) obtained from ISP; substituted polyacrylamides; polyethyleneimine, polypropyleneimine and substituted derivatives; polyamine homopolymers (Golchem CL118); polyamine co-polymers (ege.g. condensates of epichlorohydrin and mono or dimethylamine); polydiallyl dimethyl ammonium chloride (polyDADMAC); substituted dextrans; modified guar gum (substituted with hydroxypropyltrimonium chloride); substituted proteins (ege.g. quaternary groups substituted on soya protein and hydrolysed collagen); polyamino acids (ege.g. polylysine); low molecular weight polyamino compounds (ege.g. spermine and spermidine). Natural or artificial polymers may be employed.

Cationic polyelectrolytes with MW 150 to 5,000,000, preferably 5000 to 500,000, more preferably 5000 to 100,000 may be employed. An amount of 0.01 to 10% is preferred, more preferably 0.1 to 2%, especially 0.05 to 5% w/v.

The anionic polyelectrolyte is preferably a polymer with anionic groups distributed along the molecular chain. The anionic groups, which may include carboxylate, sulphonate, sulphate or other negatively charged ionisable groupings, may be disposed upon groups pendant from the chain or bonded directly to the polymer backbone. Natural or artificial polymers may be employed.

Examples of anionic polyelectrolytes include: Gantrez (Sseries, AN-series); alginic acid and salts; carboxymethyl celluloses and salts; substituted polyacrylamides (e.g. substituted with carboxylic acid groups); polyacrylic acids and salts; polystyrene sulphonic acids and salts; dextran sulphates; substituted saccharides ege.g. sucrose octosulphate; heparin. Anionic polyelectrolytes with MW of 150 to 5,000,000 may be used, preferably 5000 to 500,000, more preferably 5000 to 100,000. An amount of 0.01% to 10% is preferred especially 0.05 to 5% more especially 0.1 to 2% w/v.

A particular preferred stabilizer is N-acetyl cysteine in an amount of 0 to 10%, preferably 0.01 to 5%.

Further the composition may contain any preservative like e.g. phenoxyethanol, isothiazoline, sorbic acid or any other suitable preservative known to skilled persons.

The composition may further preferably comprise any buffering agent. All of the commonly known buffering agents may be used, like Tris/HCl, $K_2HPO_4/KH_2PO_4$, $Na_2HPO^4/NaH_2PO_4$, MOPS (3-(N-morpholino)propanesulfonic acid), HEPES (4-2-hydroxyethyl-1-piperazineethanesulfonic acid), TAPS (3-{[tris(hydroxymethyl) methyl]amino} propanesulfonic acid), Bicine (N,N-bis (2-hydroxyethyl)glycine), Tricine (N-tris(hydroxymethyl) methylglycine), TES (2-{[tris(hydroxymethyl)methyl] amino} ethanesulfonic acid), PIPES (piperazine-N,N'-bis(2-ethanesulfonic acid)), SSC (saline sodium citrate), MES (2-(N-morpholino)ethanesulfonic acid) without being limited to these.

Suitable solvents in the composition according to the invention are preferably water or aqueous solutions, organic solvents like alcohol, preferably ethanol, or polyethyleneglycol (PEG). Mixtures of said solvents as well can be used. Further natural oils may be used as a solvent for some of the ingredients and the composition may be provided as an emulsion. A particularly preferred solvent is water or an aqueous solution.

Antioxidants useful for the present composition may be e.g. vitamin C, vitamin E, flavonoids, carotinoids, or salts or derivatives thereof.

Preferred film-forming agents are such agents commonly used in cosmetic application, like e.g. Acrylamide/Sodium, Acrylate Copolymer, Acrylates/Acrylamide Copolymer, Butyl Ester of PVM/MA Copolymer, Carboxymethyl Chitin, Chitosan, Hydroxypropyl Cellulose, Polyquatemium-36, PVP, PVP/VA Copolymer, VA/Crotonates Copolymer or Vinyl Caprolactam/PCP/Dimethylaminoctyl Methylacrylate Copolymer.

All the above mentioned additives may be present in an amount of 0 to 20, preferably 0.001, 0.01, 0.05 or 0.1 to 10, more preferably 0.5 to 5% (w/v), if not otherwise stated above.

If desired, further additives may be present, in particular in an amount of 0 to 20, preferably 0.1 to 20, preferably 0.2 to 15, particularly 0.5 to 10 wt.-%. Preferred additives are nutrients for cells. They can be selected from glucose, e.g. in amounts of 0.1 to 5 wt.-%, insulin in amounts of up to 25 IU/ml, the natural amino acids, in particular cysteine, e.g. 0.1 to 5 wt.-%, or tissue factors, such as interleukins in physiological amounts, up to a 10-fold amount thereof.

Preferably the composition represents an aqueous solution comprising
(a) an oxygen carrier, preferably hemoglobin or myoglobin, and
(b) at least one further ingredient, selected from electrolyte(s) preservative(s), stabilizer(s), anti-flocculant(s), anticoagulant(s), pH buffering agent(s), antioxidant(s), organic solvent, film-forming agent(s) and crosslinking agent(s).

In a particular preferred embodiment the composition represents an aqueous solution comprising (a) an oxygen carrier, preferably hemoglobin or myoglobin, wherein in at least 40% of said oxygen carrier the oxygen binding site is charged by a non-O2 ligand, and (b) at least one further ingredient, selected from electrolyte(s) preservative(s), stabilizer(s), anti-flocculant(s), anticoagulant(s), pH buffering agent(s), antioxidant(s), organic solvent, film-forming agent(s) and crosslinking agent(s).

In a preferred embodiment of the present invention the composition comprises an oxygen carrier, which is isolated from whole blood of a human or animal, preferably from pigs.

It is suitable that the oxygen carrier usable for the composition of the present invention is isolated/purified from whole blood.

In a preferred embodiment for preparation of the composition the oxygen carrier is isolated from blood of a human or animal and is further purified to be essentially free of plasma and cellular membrane constituents.

With "essentially free" is meant that the considered compound or composition doesn't comprise more than 20%, preferably not more than 10%, even more preferred not more than 5% and particularly preferred not more than 2% or less than 1% of the mentioned undesired compound(s).

The purification can comprise any suitable means or method steps, like e.g. selective lysis or precipitation, centrifugation, ultracentrifugation, fractionated centrifugation, chromatography methods like anion exchange chromatography, size exclusion chromatography, affinity or adsorption chromatography, gel filtration or molecular sieve chromatography, or dialysis, without being restricted to these examples, as far as by the applied methods the oxygen carrier is denaturated as less as possible. Preferably during isolation and purification the oxygen carrier remains essentially in solution.

When the oxygen carrier is isolated from whole blood, it is preferred that either the cells comprising the oxygen carrier are separated from other blood components or said cells are selectively lysed to deliver the (soluble) oxygen carrier into solution and thereafter the non-soluble components are separated. A combination of the two methods as well is suitable. The lysis of the oxygen carrier containing cells may be carried out by any suitable lysis method, e.g. chemical lysis, osmotical lysis, mechanical lysis, thermal lysis or similar.

Cell debris may be separated by any suitable means or method. This includes e.g. centrifugation, filtration, sedimentation and decantation, dialysis or any similar method.

For separating non-lysed cells or the cell debris from the solved oxygen carrier a common method is pelletation of the solid material. For example a centrifugation step may be carried out. Centrifugation with 2 to 5000×g usually is sufficient for pelleting cells and cell debris.

For pelleting further non-solved components, e.g. any precipitate developed during the purification process, at, at any time during the purification process further centrifugation steps may be carried out, in particular centrifugation steps using higher forces, up to ultracentrifugation with up to $10^6 \times g$.

The purification of the oxygen carrier containing solution additionally or as an alternative to any centrifugation step may comprise at least one filtration step, preferably at least two, three or more filtration steps. This can be carried out either by using at least one, preferably at least two, more preferably at least three filters (if more than one filter is used in the present application we use the term "filter cascade"), or by one, two, three or more separate filtration steps.

Said filter cascade or the different filtering steps may include two, three, four, five ore more filters of different type, different material and or different pore sizes. Further a deep bed filter like e.g. glass wool or similar may be used, preferably as a first filter material to retain coarse cell debris. If more than one filter is used, it is preferred to use filters providing different pore diameters in decreased order. For example, if three different filters are used, the first filter (after the deep bed filter) may have an average pore size of 1 to 0.5 μm, the second filter may have a pore size of 0.7 to 0.3 μm and the third a pore size of 0.4 to 0.1 μm, wherein independent from the overlapping ranges cited before the following filter in any case has a smaller pore size than the filter prior to that. By said filtering step(s) solid and precipitated material having a larger size than the pore size of the used filters is essentially removed.

Further an ultrafiltration step may be included in the purification process for purifying the oxygen carrier(s). By such an ultrafiltration step non-desired solved macromolecules can be separated. Preferably the size exclusion limit is selected to separate macromolecules which are bigger (larger, higher molecular weight) than the desired oxygen carriers, accordingly said macromolecules are retained by the filter. Due to the molecular weight of hemoglobin of about 64,000 Dalton the size exclusion limit of the ultrafiltration filter should be higher. To make sure that the yield of hemoglobin is not decreased by the ultrafiltration step, it is preferred to select the size exclusion of the filter at about 100,000 Dalton, preferably at about 200,000 Dalton, more preferred at about 300,000 Dalton without being restricted to these values.

Additionally or as an alternative any suitable chromatography step can be carried out. A particularly preferred type of chromatography is ion exchange or size exclusion chromatography.

The same result may be obtained by a dialysis step using a dialysis membrane providing the above mentioned size exclusion limits, allowing the oxygen carrier to pass, but retaining the macromolecules having a higher molecular size.

To lower the amount of small molecular weight compounds in solution an additional dialysis step may be carried out using a dialysis membrane having a size exclusion limit of about 50.000 Dalton, allowing smaller molecules to pass, but retaining the oxygen carrier.

To diminish the virus and/or microorganism contamination in the composition it is particularly preferred to include a step of virus content degradation in the purification process. The virus content is reduced by this step, preferably to a burden of less than 10, preferably less than 5, more preferably less than 2 virus particles per ml, and even more preferred to 0. In this step it is preferred that the solution comprising the oxygen carrier is passed through a virus content degradation filter ("virus filter"). Such filters are commonly known and available on the market. Examples are Sartorius Virosart® CPV, Planova® 15N, 20N, 20N, Millipore Viresolve® NFP or PALL Pegasus® Grade LV6, without being limited to these. Alternatively or additionally, preferably after the passage through the filter, a treatment with UV light, in particular UV light of a wavelength of 245 nm may be applied to dispatch any remaining viruses.

Optionally at any stage during the process of isolation of the oxygen carrier at least one heating step may be carried out. This step comprises the heating of the oxygen carrier containing suspension or solution during the isolation procedure to a temperature in the range of 40 to 85° C., preferably 60 to 80° C., more preferred in the range of 65 to 75° C. The heating step is carried out preferably for 10 min to 6 hours, preferably for 20 min to 4 hours and most preferred for 30 min to 3 hours and may comprise several different temperatures within the before mentioned range.

According to the process of the present invention it is preferred that the oxygen carrier remains in solution during the whole purification process. Further it is preferred that the oxygen carrier remains in solution during the whole purification process and during preparation of the composition of the present invention. This means that it is preferred that the oxygen carrier is not precipitated in the process of the present invention and accordingly remains in its natural three-dimensional structure as present in its natural environment.

In a particular preferred process according to the present invention the process for purifying an oxygen carrier from whole blood comprises at least the steps:

(a) separating plasma of the whole blood
(b) lysing the red blood cells
(c) optionally, but preferably charging the oxygen carriers with a ligand
(d) heating the sample to a temperature in the range of 40 to 85° C.

(e) separating the oxygen carrier from any non-desired blood components.

By these steps an oxygen carrier containing solution is obtainable which can be used for the method of treatment and/or for the preparation of the composition of the present invention. In particular the oxygen carrier containing solution obtainable by these steps may be concentrated to a desired amount of the oxygen carrier and to this solution the at least one further ingredient(s) is/are added to obtain the composition of the present invention.

Step (a) of the present method can be carried out by any of the commonly used methods for separating plasma from whole blood, preferably by centrifugation or filtration. By centrifugation for about 30 min at about 2000 to 5000 rpm, e.g. 4000 rpm red blood cells are pelleted, whereas soluble compounds and white blood cells remain predominantly in the supernatant. By repeating resuspension and pelleting of the red blood cells e.g. 2 to 5 times, separation of the red blood cells from the undesired blood compounds can be increased.

Step (b) is preferably carried out by adding water, preferably distilled water or a suitable sub-isotonic buffer, preferably a phosphate buffer, to the thickened blood of step (a). After lysing the red blood cells with water or a sub-isotonic buffer preferably a salt is added to the solution/suspension to obtain physiological concentration of said salt in solution. Preferably NaCl is added to an amount of 0.9% in solution.

Optional step (c) may be carried out after step (a), after step (b), after step (d) or after step (e), but is preferably carried out at least after step (b). It is particularly pointed out that step (c) is not necessarily carried out immediately as a next step after step (b), but as well can be carried out or repeated after step (d), after step (e) or any following treatment steps. The charging of the oxygen carrier in the solution/suspension may be carried out by introducing gas in the solution/suspension, preferably CO or NO gas or a mixture thereof. In a preferred embodiment CO gas is introduced into the solution/suspension for a time period long enough to obtain a >90% saturation in the solution/suspension, preferably a >95% saturation.

Step (d) may be carried out after step (a), after step (b), after step (c) or after step (e), but is preferably carried out after step (c). Further the heating can be repeated during the isolation procedure. This step comprises the heating of the oxygen carrier containing suspension or solution during the isolation procedure to a temperature in the range of 40 to 85° C., preferably 60 to 80° C., more preferred in the range of 65 to 75° C. The heating step is carried out preferably for 10 min to 6 hours, preferably for 20 min to 4 hours and most preferred for 30 min to 3 hours and may comprise several different temperatures within the before mentioned range.

In step (e) the oxygen carrier is purified from further non-desired ingredients still contained in solution, like non-lysed cells, cell debris, any precipitate or other non-soluble ingredients. Further the oxygen-carrier may be further purified by separating at least partially non-desired soluble compounds, like e.g. soluble macromolecules or soluble compounds having low molecular weight.

Accordingly said step (e) may include several single steps, like filtration, ultrafiltration, centrifugation, ultracentrifugation, chromatography, dialysis using different types of dialysis membranes providing different size exclusion limits, washing steps, concentration of the oxygen carrier content etc. . . . Any of the methods cited above may be included in this purification step.

Preferably at least one centrifugation and/or at least one filtration step is comprised in step (e). E.g. the lysate may be spinned in a centrifuge to separate remaining cells and cell debris or it is filtered e.g. by a filter cascade as described above. The lysate can be as well first centrifuged and thereafter filtered, or it may be filtered in a first step through a deep bed filter and thereafter through at least one filter or a filter cascade. By the centrifugation or the deep bed filter the handling during any following filtering steps is simplified due to less material settling on and clogging the filter(s). If not a filter cascade is used, it is preferred that at least one filter is used allowing to retain essentially all of the solid materials contained in the suspension and allowing to pass all the solved components. In a more preferred embodiment at least one of the used filter(s) is able to retain as well microorganisms, acting as a sterile filter. Further preferred an ultrafiltration step and/or a step for diminishing the virus and/or microorganism content of the solution can be carried out. Accordingly it is preferred that after step (e) the oxygen carrier containing solution is essentially free of any non-solved particles, flocks or precipitate.

In step (e) additionally to any of the steps/methods cited above the solution comprising the desired oxygen carrier may be washed and/or concentrated. By "washing" is meant that molecules smaller than the desired oxygen carrier (having lower molecular weight) are separated, preferably by adding the same or a multifold (e.g. 5 to 10 fold) amount of an isotonic solution to the oxygen carrier containing solution and thereafter filtering the obtained (diluted) solution by a filter retaining the oxygen carrier and allowing smaller molecules to pass. For washing the solution preferably a 0.9% NaCl solution is used. The washing step may be repeated 2 or 3 or 4 or 5 or up to 10 times. A preferred embodiment is exemplified by the use of a filter having a size exclusion limit of 5,000 Dalton, 10,000 Dalton or 20,000 Dalton, allowing smaller molecules to pass. In this step the oxygen carrier containing solution (preferably after washing) may be concentrated to a desired concentration of the oxygen carrier, e.g. to a concentration of 50 g/l, 100 g/l or 200 g/l without being restricted to these amounts. Any desired concentration can be obtained either by concentrating by filtration or by adding 0.9% NaCl or a similar isotonic solution.

The so obtainable oxygen carrier containing solution can then be used in a method for reducing undue scarring of a wound or wound area or to prepare a composition which according to the present invention can be used in a method for reducing undue wound scarring.

In a preferred embodiment the composition usable according to the present invention is prepared by adding to the oxygen carrier containing solution at least a preservative, preferably a pharmaceutically acceptable preservative like e.g. phenoxyethanol, parabenes, sodium benzoate, benzyl alcohol, hexachlorophen and an antioxidant and/or stabilizer like e.g. N-acetylcysteine, sodium octanoate, N-acetyl-1-tryptophanate, N-acetyl-methioninate, vitamin E, vitamin C, methyl prednisolone or mannitol. Additionally any of the further ingredients described above may be added additionally.

The finished composition may be sterilized again, if desired, e.g. by heating, filtration, centrifugation, addition of preservatives, vapour application, gas application or UV-application or a combination of at least two of them, preferably by a further sterile filtration step and is preferably filled in sterile containers or sterile bags for storing.

According to a preferred embodiment the sterile bags are positioned in an aerosol can for later use. One example can be a Bag-on-Valve system, comprising a bag, e.g. a laminated aluminium bag and an aluminium or tin plate aerosol can. Due to the separation of product and propellant, Bag-on-Valve can be used with compressed air or nitrogen at a pressure e.g. from 2 to 9 bar.

According to the invention, the composition is preferably used in a method of to reduce the formation of undue scarring during treatment of open wounds, preferably chronic wounds of humans and animals or burn wounds. In particular such wounds can be effectively treated which are characterized by deep, large or extensive wound areas with disrupted skin integrity and/or tissue erosion, e.g. lack of tissue or skin, damage of tissue or skin or similar. The new tissue or skin formed during the treatment of the wound (area) is considerably less scarred and resembles more uninjured/unwounded tissue or skin than scars.

"Undue scarring" according to the present invention means that the new tissue formed on the wound may be thick, rigid and/or less elastic (brittle), maybe rough, fissured and optionally braking again (relapse or recrudescence), whereas a nicely healed wound according to the invention results in a tissue which is more comparable to unwounded skin or tissue, which means resilient, smooth, elastic, showing less to no recrudescences. In particular the newly built tissue or skin on wound areas with disrupted skin integrity or tissue erosion is elastic (less brittle) and non-fissured.

Surprisingly it was found that the oxygen carriers improve scarring, which means that the tissue or new skin formed due to the healing of the wound is less scarred but more similar to unwounded tissue or skin.

As described above scarring is often undue under decreased oxygen supplement. It appears therefore logic that the formation of new tissue on wounds requires the oxygen-charged oxygen carriers. However, according to the present invention it was found that it is as well possible to obtain a positive result in scarring by applying an oxygen-carrier charged with CO or NO. Without being bound our theory is that due to the oxygen partial pressure in air the ligand may be replaced by oxygen when applied to the wound and accordingly the scarring is diminished.

Treatment of wounds with the oxygen carrier results in less rigid, smooth, resilient new tissue. The composition including the charged oxygen carrier has the further advantage of increased stability of the oxygen-carrier due to its non-oxidized status based on the charge with the CO or NO ligand resulting in a good preparation and storing stability. The oxygen carrier or the composition is easy to apply and good to handle and provides a safe and effective approach to improve (decrease) scarring by facilitated diffusion mediated by the oxygen carrier/agent into the healing area.

The oxygen carrier or the composition of the present invention is applied externally. Depending on the state of the wound, it is applied on, preferably sprayed on the wound area in form of a fine spray, or it is applied to a tissue, bandage (such as an adhesive bandage) or patch applied to the wound area.

Preferably the oxygen carrier is applied on the wound by spraying an aqueous composition comprising said oxygen carrier, preferably a CO-charged haemoglobin or myoglobin, on the open wound and applying thereafter a tissue, bandage or patch on the treated wound. Alternatively, on particular when a person is sensitive to the spray puff, the composition comprising said oxygen carrier, preferably a CO-charged haemoglobin or myoglobin, is applied on a tissue, bandage or patch and said tissue, bandage or patch is then applied to the wound area. Alternatively, but less preferred, said tissue, bandage or patch can be first applied to the wound and then impregnated with the oxygen carrier comprising composition.

If a wound is reaching deep into the sub-epidermal tissue, like e.g. in case of decubitus ulcers (pressure ulcers) a tissue, pad or tampon can be introduced into the wound after spraying the oxygen carrier comprising composition into the wound, or a tissue, pad or tampon impregnated with the oxygen carrier comprising composition at least on the surface contacting the wound area can be introduced into the open wound to allow as much wound surface as possible to be in contact with the oxygen carrier.

Applying the composition comprising said oxygen carrier to the tissue, bandage, patch, pad or tampon or any other suitable medical device can be done by contacting, e.g. spraying, dipping or immersing, the tissue, bandage, patch, pad or tampon or any other suitable medical device with the composition.

In all these cases it is particularly preferred to apply an aqueous composition comprising CO-charged haemoglobin, in particular an aqueous composition as described above, and most preferably a composition as prepared in Example 1, onto the open wound and thereafter applying a sterile tissue, bandage, patch, pad or tampon or any similar suitable medical device to the so treated wound, or to apply said CO-charged haemoglobin comprising composition onto a sterile tissue, bandage, patch, pad or tampon or any similar suitable medical device and then applying said medical device onto/into the wound area.

The wound treatment preferably is done at least once a day, preferably in the morning, or twice a day, e.g. in the morning and evening, whereas it is preferred that at least 8 hours, preferably at least 10 hours are between two treatments.

According to the invention, it has been shown that scarring of open wounds, in particular of chronical wounds can be decreased during healing of said wounds, resulting in a tissue very similar to unwounded tissue or skin. The treated wounds can be wounds after operations, after trauma, after injuries, wounds with poor healing or hypoxic wounds, or also wounds caused by degenerative changes in the tissue. In this connection, they can be wounds caused by degenerative changes of the arterial blood vessels and wounds resulting from chronic venous insufficiency. These particularly include decubitus as well as chronic wounds, particularly those resulting from diabetes. Further wounds caused by burn (either by heat, by chemicals or by freezing) or by scalding can be effectively treated.

EXAMPLES

Example 1

Hemoglobin was isolated from whole blood of pigs by separating the red blood cells from serum, lysing the collected red blood cells, pelleting cell debris, charging the hemoglobin with CO by introducing CO gas until saturation of the liquid sample is obtained, carrying out several filtration steps, including a virus filtration step and washing the obtained hemoglobin solution by adding twice a 2-fold volume of 0.9% saline and filtering the solution.

A ready-to-use composition for wound treatment was prepared, comprising 10% of purified and stabilized hemoglobin, 0.05% N-acetyl cysteine and 0.7% phenoxy ethanol in ethanol in 0.9% NaCl. The composition was charged again with CO gas, separated into 10 portions and packaged into an aerosol can, respectively.

Example 2

A second portion of hemoglobin was isolated from whole blood of pigs by the same method as described in Example 1, but without charging the hemoglobin with CO during preparation.

A ready-to-use composition for wound treatment was prepared, comprising 10% of purified hemoglobin, 0.05% N-acetyl cysteine and 0.7% phenoxy ethanol in ethanol in 0.9% NaCl. The composition was separated into 10 portions and packaged into an aerosol can, respectively.

Example 3

An 80 years old female patient had two chronic wounds (Ulcus cruris venosum) at the lower leg for more than 1 year. One wound was treated with hemoglobin spray of Example 1 for 4 months (3 times/week) while the second wound was treated conventionally without hemoglobin spray.

The wound treated with hemoglobin showed a faster wound healing although the wound was significantly larger than the wound without hemoglobin treatment. Surprisingly, the scar tissue obtained on the wound treated with hemoglobin spray during the wound healing process revealed to be more resilient and less scarred than the tissue formed on the wound treated without hemoglobin.

According to an internal score for the quality of the scar tissue (0-10, 10, wherein 0=no wound healing, 1=no elasticity, high risk of relapse, 10=normal tissue (never wounded)) the wound without hemoglobin treatment was qualified at 4 while scar tissue of the wound with hemoglobin treatment was valued at 7.

Example 4

A 20 year old male patient having a large acute wound due to burning (Grade 2a/b) was treated first conventionally with Silver-Sulfadiazine. After 7 days of treatment, the wound showed no significant improvement. Treatment was changed and hemoglobin spray prepared as described above was applied to the wound once daily. After 7 days of treatment the patient was relieved from the hospital, wound treatment was continued at home. The scar tissue obtained was obviously more resilient, smoother and more elastic than obtained in other cases of burn wounds treated with a conventional state of the art treatment regime.

According to an internal score for the quality of the scar tissue (0-10, wherein 0=no wound healing, 1=no elasticity, high risk of relapse, 10=normal tissue (never wounded)) the scar tissue of the wound with hemoglobin treatment was valued at 7, whereas conventionally treated burn wounds result in a score of 3 to 4.

Example 5

Several male patients (age 65-75) with Diabetic foot ulcer at the lower leg were treated for three months with hemoglobin spray according to Example 1 (stored at 10° C. for 6 months) or a freshly prepared hemoglobin spray according to Example 2 (storage at 4° C. for 3 days max.) until complete wound healing was obtained. According to the attending dermatologists, the scar tissue obtained showed in all cases an improved elasticity and smoothness in comparison to wounds treated by the conventional treatment regime without hemoglobin spray. It was confirmed that the quality of the scar tissue is important for the relapse rate of a healed wound.

According to an internal score for the quality of the scar tissue (0-10, 10, wherein 0=no wound healing, 1=no elasticity, high risk of relapse, 10=normal tissue (never wounded)) the scar tissue of the wounds treated with CO-loaded hemoglobin prepared according to Example 1 (4 subjects) were) were valued at 7-8, wounds treated with unloaded fresh prepared hemoglobin according to Example 2 (2 subjects) were valued at 6 in comparison to 4 for wounds treated conventionally.

Example 6

When slough (a combination of dead white cells, dead bacteria, rehydrated necrotic tissue and fibrous tissue) attaches to the granular base of a wound, it provides an optimum environment for bacterial growth, infection and increased exudate. Hunt describes a study in which 100 patients with sloughy wounds were treated with twice-weekly administrations of CO-charged haemoglobin spray in a community setting. See Hunt, "Topical oxygen-haemoglobin use on sloughy wounds: positive patient outcomes and the promotion of self-care," in Wounds UK, vol. 11, No. 4, 2015. Hunt reported that after four weeks, "all wounds had demonstrated positive measured endpoints (100%) and continued wound size reduction (99%), with 100% of patients and carriers finding the product easy to use and having an overall positive wound care experience.

What is claimed is:

1. A method of decreasing undue scarring of healing wounds and/or lowering the relapse rate of wounds, the method comprising applying an aqueous composition comprising hemoglobin on the wound area, wherein at least 40% of the hemoglobin is provided in CO-charged form, and wherein a spray of the aqueous composition is applied to the wound area in an ambient environment and does not need to be applied in an atmosphere of pure oxygen for effectiveness.

2. The method of claim 1, wherein at least 50% of the hemoglobin is provided in CO-charged form.

3. The method of claim 1, wherein at least 60% of the hemoglobin is provided in CO-charged form.

4. The method of claim 1, wherein at least 70% of the hemoglobin is provided in CO-charged form.

5. The method of claim 1, wherein at least 80% of the hemoglobin is provided in CO-charged form.

6. The method of claim 1, wherein at least 90% of the hemoglobin is provided in CO-charged form.

7. The method of claim 1, wherein at least 95% of the hemoglobin is provided in CO-charged form.

8. The method of claim 1, wherein the hemoglobin is in the form of a fine spray from an aerosol can.

9. The method of claim 1, wherein the composition is applied to a tissue, bandage, patch, pad or tampon, which is then applied to the wound area.

10. The method of claim 1, wherein the wounds to be treated are at least one of chronic wounds, operation wounds, injury wounds, wounds after trauma, open wounds, wounds with poor healing, hypoxic wounds, wounds arising from degeneration or stenosis of arterial blood vessels, wounds from diabetes disease, wounds from chronic venous insufficiency, decubitus ulcer wounds, heat burn wounds, chemical burn wounds, freezing burn wounds, scalding wounds, or sloughy wounds.

The composition can be stored between 4° C. and room temperature for months to years.

11. The method of claim 1, wherein the composition further comprises at least one further ingredient, selected from electrolyte(s), preservative(s), stabilizer(s), anti-flocculant(s), anticoagulant(s), pH buffering agent(s), solvent(s), antioxidant(s), film-forming agent(s) and crosslinking agent(s).

12. The composition of claim 1, wherein the hemoglobin is provided in sterilized form.

13. The composition of claim 1, wherein the hemoglobin is naturally occurring hemoglobin of human or animal origin, or is artificially treated, crosslinked or modified hemoglobin of human or animal origin.

* * * * *